US009517339B2

(12) United States Patent
Koceja et al.

(10) Patent No.: US 9,517,339 B2
(45) Date of Patent: Dec. 13, 2016

(54) METHOD AND SYSTEM FOR TRAINING AN INDIVIDUAL

(71) Applicant: Indiana University Research and Technology Corporation, Indianapolis, IN (US)

(72) Inventors: David Koceja, Indianapolis, IN (US); Behdad Tahayori, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 14/769,120

(22) PCT Filed: Feb. 3, 2014

(86) PCT No.: PCT/US2014/014400
§ 371 (c)(1),
(2) Date: Aug. 20, 2015

(87) PCT Pub. No.: WO2014/130228
PCT Pub. Date: Aug. 28, 2014

(65) Prior Publication Data
US 2015/0374981 A1    Dec. 31, 2015

Related U.S. Application Data

(60) Provisional application No. 61/766,739, filed on Feb. 20, 2013.

(51) Int. Cl.
*A61N 1/00*        (2006.01)
*A61N 1/36*        (2006.01)
*A63B 22/14*       (2006.01)

(52) U.S. Cl.
CPC ....... *A61N 1/36003* (2013.01); *A61N 1/36014* (2013.01); *A63B 22/14* (2013.01)

(58) Field of Classification Search
CPC .. A61N 1/36; A61N 1/36003; A61N 1/36014; A63B 22/14; A63B 22/16
See application file for complete search history.

(56) References Cited

U.S. PATENT DOCUMENTS 4,738,269 A * 4/1988 Nashner ............... A61B 5/1036
                                                    434/258
6,063,046 A    5/2000 Allum
8,249,714 B1   8/2012 Hartman et al.
(Continued)

OTHER PUBLICATIONS

International Searching Authority, International Search Report and Written Opinion for PCT/US2014/014400, dated May 27, 2014, 9 pages.

(Continued)

*Primary Examiner* — Robert N Wieland
(74) *Attorney, Agent, or Firm* — Faegre Baker Daniels LLP

(57) ABSTRACT

A method of training an individual includes receiving data indicative of a training suitability state of an individual upon a tiltable support platform, and commanding electrical stimulation of a spinal reflex pathway innervating a muscle in the individual, responsive to the data, and such that the muscle reflexively contracts to tilt the support platform. A value indicative of an amplitude of the reflexive contraction is electronically recorded.

17 Claims, 2 Drawing Sheets

(56) References Cited

U.S. PATENT DOCUMENTS

| | | | |
|---|---|---|---|
| 2002/0011250 A1* | 1/2002 | Stewart | A61B 5/00 128/898 |
| 2003/0109365 A1 | 6/2003 | Smith | |
| 2008/0208287 A1* | 8/2008 | Palermo | A61N 1/0452 607/48 |
| 2011/0319238 A1 | 12/2011 | Sandvikmoen | |

OTHER PUBLICATIONS

International Searching Authority, Written Opinion for PCT/US2014/014400, dated May 27, 2014, 2 pages.

* cited by examiner

METHOD AND SYSTEM FOR TRAINING AN INDIVIDUAL

CROSS-REFERENCE TO RELATED APPLICATIONS

This application is a U.S. National Phase Patent Application based on International Application No. PCT/US2014/014400 filed Feb. 3, 2014, which claims the benefit of the filing date of U.S. Provisional Patent Application Ser. No. 61/766,739, filed May 1, 2013.

TECHNICAL FIELD

The present disclosure related generally to the field of therapeutic training, and relates more particularly to electrically stimulating a spinal reflex pathway in an individual upon a tiltable support platform, and recording a value indicative of an amplitude of an induced reflexive muscle contraction.

BACKGROUND

A wide variety of systems and techniques are used in therapeutically training and evaluating individuals. Those skilled in the art will be aware of various apparatuses used in physical therapy and related research fields. In the case of individuals have certain types of neurological damage, a notable example being stroke patients, the individual's ability to balance while standing or walking can often be compromised. It has been discovered that an apparatus known in the art as a "tilt board" can be used to train an individual to improve their balance. Conventional tilt boards have a platform supported upon a relatively narrow ground contacting base or set of bars, legs, etc. An individual is typically tasked with standing on the tilt board, and compensating for the instability inherent in the narrow base, especially when their balance has been externally perturbed. It has been observed that over time certain individuals can improve their ability to balance, and thereby improve their overall quality of life and personal safety.

One application of tilt boards employs an external electrical stimulation of a muscle in the individual's leg, commonly the soleus. The external stimulation induces the soleus muscle to contract, redistributing the body weight of the individual upon the tilt board, causing the tilt board to tilt, and requiring the patient to compensate and return the tilt board to a more or less horizontal orientation. Through repetition of this general technique, certain individuals commonly assisted by a trainer, can improve their balance, apparently due to inhibition of the reflexiveness of their response to being tipped off balance. Despite some success in training such individuals over the years, there remains ample room for improvement.

SUMMARY OF THE INVENTION

In one aspect, a method of training an individual includes receiving data indicative of a training suitability state of an individual upon a support platform, where the support platform is tiltable in response to contraction of a muscle in the individual's body redistributing the individual's body weight upon the support platform. The method further includes commanding electrical stimulation of a spinal reflex pathway innervating the muscle in the individual, responsive to the data, and such that the muscle reflexively contracts to tilt the support platform. The method further includes electronically recording a value indicative of an amplitude of the reflexive contraction.

In another aspect, a system for training an individual includes a support platform configured to support an individual for training, and tiltable in response to contraction of a muscle in the individual's body redistributing the individual's body weight upon the support platform. The system further includes a plurality of sensing mechanisms configured to monitor a plurality of training suitability parameters, and an electrical stimulation mechanism configured to electrically stimulate a spinal reflex pathway in the individual. The system further includes a computing device configured to receive data from the plurality of sensing mechanisms indicative of a training suitability state of the individual, and being in control communication with the electrical stimulation mechanism. The computing device is further configured to command electrical stimulation of the spinal reflex pathway responsive to the data, such that the muscle reflexively contracts to tilt the support platform, and to record a value indicative of an amplitude of the reflexive contraction.

DETAILED DESCRIPTION

Figure 1:
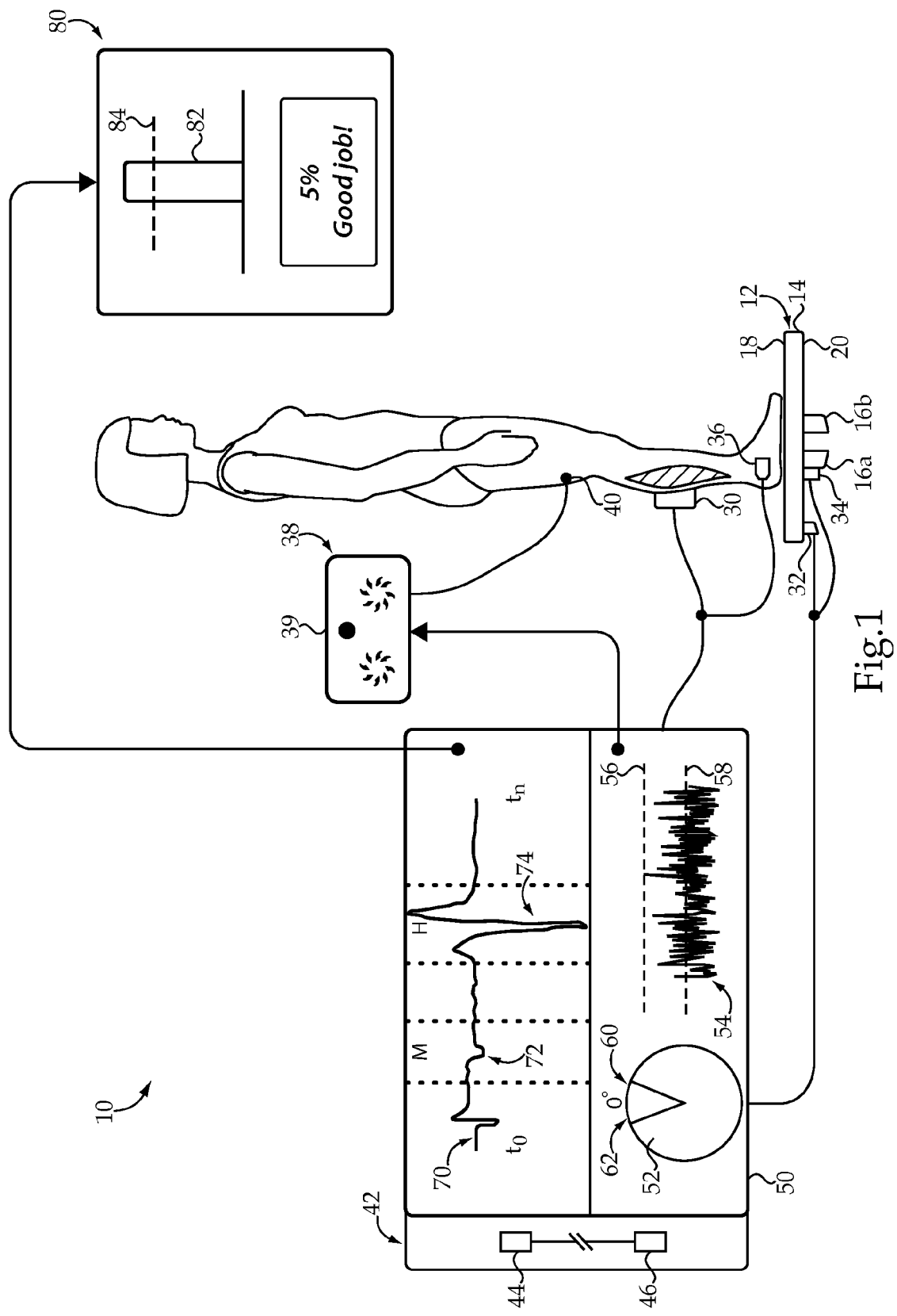
FIG. 1 is a diagrammatic view of a system for training an individual, according to one embodiment.

Referring to FIG. 1, there is shown a system 10 for training an individual according to one embodiment. The individual may be an elderly subject having reduced ability to suppress spinal reflexes, such as the soleus H-reflex, a subject with postural instability associated with cerebellar dysfunction and having analogous reflex suppression problems, or a variety of other subjects having a range of conditions which those skilled in the art will recognize may benefit from the teachings set forth herein. The individual might also be a healthy subject who is trained within the scope of the present disclosure for research or evaluation purposes. System 10 may include a support platform 12 configured to support an individual for training, and having a deck 14 with an upper standing surface 18 for supporting the individual thereon, a lower surface 20, and a first and second elongate support bar 16a and 16b, respectively, mounted to lower surface 20. Platform 12 may be tiltable in response to contraction of a muscle in the individual's body, such as the soleus muscle in one or both of the individual's legs, redistributing the individual's body weight upon platform 12. As will be further apparent from the following description, system 10 may be uniquely configured to assess training suitability of an individual upon platform 12, and to execute a training regimen when a training suitability state exists.

To this end, system 10 may further include a plurality of sensing mechanisms configured to monitor a plurality of training suitability parameters. In a practical implementation strategy, the plurality of sensing mechanisms may include a first sensor 32 configured to monitor a tilt parameter of support platform 12, a second sensor 36 configured to monitor a muscle activity parameter of a muscle in the individual, and a third sensor 36 configured to monitor an ankle joint angle parameter in the individual. System 10 may further include a fourth sensor 34 coupled with support platform 12 and configured to monitor a stability state thereof, as further discussed herein.

System 10 may further include an electrical stimulation mechanism 38 including a generator 39 generating an electrical current, and an electrode 40 configured to electrically stimulate a spinal reflex pathway in the individual. In a practical implementation strategy, mechanism 40 may be configured to attach to the individual such as to the back of the individual's knee to electrically stimulate a sensory nerve through the individual's skin in a generally known manner. System 10 still further includes a computing device 42 configured to receive data from the plurality of sensing mechanisms indicative of a training suitability state of the individual. Computing device 42 may be in control communication with mechanism 38, and configured to command electrical stimulation of the spinal reflex pathway responsive to the data, such that a muscle such as the soleus muscle contracts to redistribute the individual's body weight upon support platform 14. The subject muscle may reflexively contract to thus tilt support platform 14. Computing device 42 may be further configured to record a value indicative of an amplitude of the reflexive contraction, for purposes which will be apparent from the following description.

Figure 2:
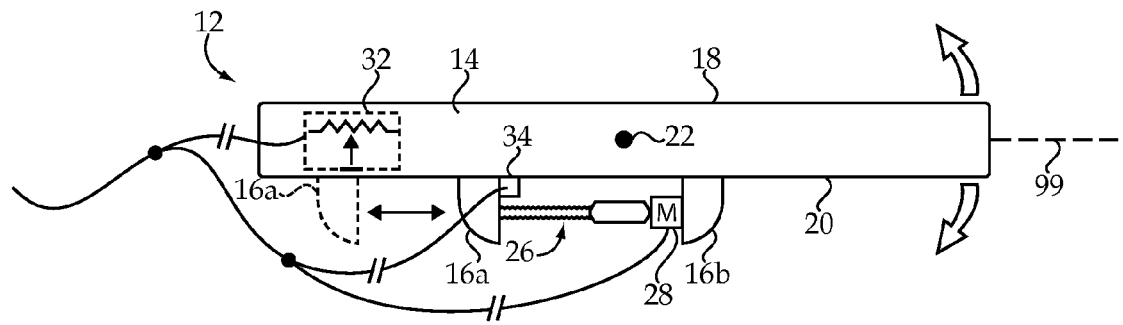
FIG. 2 is a side diagrammatic view of a tiltable support platform, according to one embodiment.

Referring also now to FIG. 2, there is shown a diagrammatic side view of support platform 12, and illustrating further features thereof. As noted above, support platform 12 may be coupled with, and typically have mounted thereon, various monitoring and control components of system 10. Sensor 32 may be one of these, and in a practical implementation strategy includes a potentiometer which outputs a signal to computing device 42 indicative of an angular displacement of support platform 12 about a horizontal axis 22, and further being indicative of a tilt angle of support platform 12 relative to a horizontal plane 99 which will typically be parallel to the ground or a facility floor upon which bars 16a and 16b are resting.

In a practical implementation strategy, support platform 12 may further include an adjustable stability varying mechanism 26 coupled with one or both of bars 16a and 16b. Bars 16a and 16b may define a clearance there between, and at least one of bars 16a and 16b may be movable relative to the other via stability varying mechanism 26. Shown in phantom in FIG. 2 is an alternate position of bar 16a which it might occupy where moved away from bar 16b to increase the subject clearance, and therefore increase a relative stability of support platform 12. It will be appreciated that axis 22 is defined by platform 12, but may have a location in three dimensional space which varies based upon positioning of support bars 16a and 16b. Mechanism 26 may include a turnbuckle mechanism in certain embodiments, and may be equipped with a motor 28 to allow a trainer or researcher to quickly and reliably adjust the positioning of bars 16a and 16b relative to one another, and thus quickly and reliably change the relative stability of support platform 12. In certain applications, this stability might be varied during a training session. Support platform 12 may also be equipped with sensor 34 to monitor a stability state of support platform 12 as determined by stability varying mechanism 26.

In one practical implementation strategy, sensor 34 might include an ultrasonic transducer mounted to support bar 16a which transmits ultrasound towards support bar 16b, and senses reflected ultrasound, and then outputs signals to computing device 42 to enable calculation of a clearance between support bars 16a and 16b based upon a time of flight of the ultrasound, which clearance is then indicative of a stability state of support platform 12. In certain instances, the "sensor" monitoring stability might be motor 28 itself. In one embodiment, support bar 16a and 16b will extend, in directions in and out of the page in FIG. 2, across at least a majority of a width of deck 14. In alternative strategies, deck 14 might be split into two parts, left and right halves, upon each of which rests one of the individual's feet. Each of the halves might be tiltable relative to one another, and have an independent stability varying mechanism enabling left side stability and right stability of support platform 12 to be independently varied. Those skilled in the art will appreciate the practical applicability of such a technique to training of individuals having asymmetric balance problems, defects, asymmetric abilities with respective to left side and right side balancing, or simply for research purposes.

Returning to FIG. 1, computing device 42 may further include a data processor 44 and a computer readable memory 46 storing computer executable program instructions for training an individual according to the present disclosure. A monitoring display 50 may be used to provide information to a trainer in real time during the course of executing a training regimen. Display 50, which could include multiple separate displays in certain embodiments, may graphically represent to a trainer various of the monitored parameters, including a tilt graphic 52 illustrating a tilt angle of support platform 12, relative to a positive tilt limit 60 and a negative tilt limit 62 defining a suitable range of tilt angles. Tilt limits 60 and 62 might be a few degrees, say, about 5° or less from the horizontal, and might be about +2° and −2°, and not readily perceptible to an observer in certain instances. Graphic 52 may thus be updated in response to data received from sensor 32. Display 50 may also illustrate a muscle activity signal trace 54 or electro-myogram (EMG), representing an electrical activity of the subject muscle relative to an upper threshold 56 and a lower threshold 58, and being updated in response to data received from sensor 30. Yet another graphic (not shown) might be provided to represent data received from sensor 36 indicative of a joint angle of an ankle joint of the individual. Sensor 36 might include a potentiometer having one part affixed to the leg of the individual, another part affixed to the foot of the individual, and having an output dependent upon displacement between the parts, or orientation of one part relative to the other part.

Display 50 may also illustrate a signal trace 70 indicative of an amplitude of the reflexive contraction induced in the muscle in response to the commanded electrical stimulation. Signal trace 70 proceeds from a time $t_0$ beginning just prior to commanding the electrical stimulation to a time $t_n$, following the end of the reflexive contraction. Between times $t_0$ and $t_n$, an M-wave response 72 may be elicited a few milliseconds subsequent to the commanded electrical stimulation, and an H-wave response, the response whose amplitude will typically be of most interest within the present context, is elicited a few milliseconds later.

As noted above, computing device 42 may record a value indicative of an amplitude of the reflexive contraction elicited by the commanded electrical stimulation. Accordingly, each time a sensory nerve of interest in the individual is stimulated, data processor 44 may record the value, such as a numerical value, on memory 46, indicative of the amplitude. During the course of a typical training session, data may be received a plurality of times indicating the individual is in a training suitability state, followed by commanding electrical stimulation of the spinal reflex pathway as described herein. During or following each of these repetitions of receiving data, and commanding electrical stimulation, computing device 42 may electronically record a value indicative of an amplitude of the reflexive contraction. This action may be understood as populating a stored history of reflexive contraction amplitudes in a plurality of repetitions over the course of a training session. As will be further apparent from the following description, executing a plurality of repetitions, and typically but not necessarily through a plurality of training sessions, an amplitude of the reflexive contraction represented by H-wave 74 signal trace 70 may be observed to reduce. In other words, the reflexiveness of the response to perturbation of the individual by way of the electrical stimulation can be observed to attenuate over time, as the individual unconsciously or semi-consciously "learns" to inhibit the reflexive response. In individuals who have problems balancing, this perturbation of their balance while standing upon support platform 12, with platform 12 bearing substantially their entire body weight, the attenuation of the reflexiveness is believed to enable improvements in balance.

System 10 may further include a feedback display 80 viewable by the individual, and displaying a bar graphic 82 or the like illustrating progress in inhibiting a reflexive muscle contraction in comparison with prior repetitions as illustrated via a baseline 84. As discussed above, computing device 42 may store a history of amplitudes of reflexive contractions, and in certain embodiments may compare a present value indicative of the amplitude of a reflexive contraction with a second value indicative of an amplitude of a reflexive contraction in at least one prior repetition, and output a display signal to display 80, responsive to the comparison. This technique is believed to facilitate so-called operant conditioning of the individual by giving them positive visual feedback. Display 80 might also include a textual graphic such as that shown FIG. 1 illustrating to the individual their relative improvement over prior repetitions.

INDUSTRIAL APPLICABILITY

Figure 3:
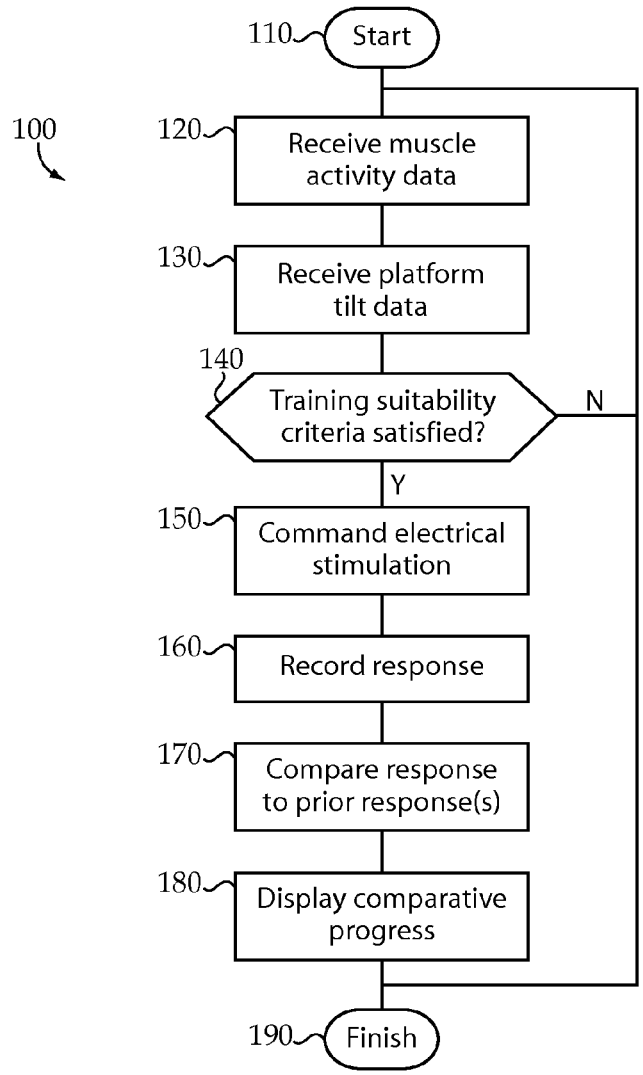
FIG. 3 is a flowchart illustrating an example process according to one embodiment.

Referring to the drawings generally, but in particular now to FIG. 3, there is shown a flowchart 100 illustrating an example training process according to one embodiment. The process of flowchart 100 begins at step 110, and proceeds to step 120 to receive muscle activity data, such as electrical activity data from sensor 30. From step 120, the process may proceed to step 130 to receive platform tilt data, such as from sensor 32. It should be appreciated that steps 120 and 130 might be executed in reverse order, or in parallel. From step 130, the process may proceed to step 140 to query whether training suitability criteria are satisfied. If no, the process may loop back to commence again, and if yes, the process may proceed to step 150. At step 140, computing device 42 may be understood as determining whether a tilt angle of support platform 12 is within a suitable range of tilt angles, such as between limits 60 and 62, and also whether muscle activity is within, or at least predominantly within, a range between thresholds 56 and 58. Data from sensor 36 might also be considered, and a determination made as to whether ankle joint angle is within a suitable range of angles.

At step 140, computing device 42 may be further understood as determining whether conditions for training are such that a desired response of the patient to electrical stimulation of the muscle can be expected to occur. The presently contemplated training techniques exploit a spinal reflex circuit commonly not compromised in certain individuals such as stroke patients, the elderly, and other patient populations who have suffered cerebral neurological damage. It has been observed that this spinal reflex pathway is neuroplastic, and an individual can learn to inhibit the amplitude of a reflexive response in this pathway through training to resist perturbations to their balance. Such plasticity can best, and perhaps only, be exploited, and balance thereby improved where suitable training conditions exist as discussed herein. Accordingly, step 140 may still further be understood as determining whether electrically stimulating the muscle will produce a response that can be exploited to take advantage of this potential plasticity, or whether factors such as tensing of the muscle by the individual, too much tilt of the support platform, too great an ankle joint angle, or still other factors exist which would be confounding. These various factors as discussed herein comprise training suitability criteria, and if satisfied, enable the process of flowchart 100 to proceed to step 150 to command the electrical stimulation. From step 150, the process may proceed to step 160 to record the induced response, for instance receiving data from sensor 130 and recording a corresponding value on memory 46. From step 160, the process may proceed to step 170 to compare the response to one or more prior responses, thenceforth to step 180 to display comparative progress to the individual via display 80, for example, and then finish at step 190.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. Other aspects, features and advantages will be apparent upon an examination of the attached drawings and appended claims.

What is claimed is:

1. A method of training an individual comprising the steps of:
   receiving data indicative of a training suitability state of an individual upon a support platform, where the support platform is tiltable in response to contraction of a muscle in the individual's body redistributing the individual's body weight upon the support platform;
   commanding electrical stimulation of a spinal reflex pathway innervating the muscle in the individual, responsive to the data, and such that the muscle reflexively contracts to tilt the support platform;
   perturbing a balance of the individual while standing, via the electrical stimulation; and
   electronically recording a value indicative of an amplitude of the reflexive contraction.

2. The method of claim 1 wherein the muscle includes the soleus muscle, and the step of commanding includes commanding electrical stimulation of a sensory nerve through the individual's skin on the back of the knee.

3. The method of claim 2 wherein the step of receiving further includes receiving data indicative of electrical activity of the muscle, and data indicative of a tilt angle of the support platform about a horizontal axis.

4. A method of training an individual comprising the steps of:
   receiving data indicative of a training suitability state of an individual upon a support platform, data indicative of electrical activity of the muscle, and data indicative of a tilt angle of the support platform about a horizontal axis, wherein the support platform bears substantially the entire body weight of the individual while standing, where the support platform is tiltable in response to contraction of a muscle in the individual's body redistributing the individual's body weight upon the support platform;

commanding electrical stimulation of a spinal reflex pathway innervating the muscle in the individual, responsive to the data, and such that the muscle reflexively contracts to tilt the support platform, wherein the muscle includes the soleus muscle, and the step of commanding includes commanding electrical stimulation of a sensory nerve through the individual's skin on the back of the knee;

perturbing a balance of the individual while standing, via the electrical stimulation; and electronically recording a value indicative of an amplitude of the reflexive contraction.

5. The method of claim 4 wherein the step of electronically recording further includes populating a stored history of reflexive contraction amplitudes in a plurality of repetitions of the receiving and commanding steps.

6. The method of claim 5 further comprising a step of comparing the value with a second value indicative of an amplitude of a reflexive contraction in at least one prior repetition of the receiving and commanding steps, and outputting a display signal to a graphical display, responsive to the comparison.

7. The method of claim 4 wherein the step of receiving further includes receiving data indicative of a joint angle in an ankle joint of the individual from a joint angle sensor coupled to the individual.

8. The method of claim 4 wherein the step of receiving further includes receiving data indicating the tilt angle is within a suitable range of tilt angles.

9. The method of claim 4 wherein the support platform includes an adjustable stability varying mechanism including a plurality of configurations each corresponding to a different stability state, and further comprising a step of receiving data from a sensing mechanism coupled to the support platform indicative of a present configuration of the adjustable stability varying mechanism.

10. The method of claim 3 wherein the step of receiving further includes receiving data indicative of a joint angle in an ankle joint of the individual from a joint angle sensor coupled to the individual.

11. The method of claim 3 wherein the step of receiving further includes receiving data indicating the tilt angle is within a suitable range of tilt angles.

12. The method of claim 1 wherein the support platform includes an adjustable stability varying mechanism including a plurality of configurations each corresponding to a different stability state, and further comprising a step of receiving data from a sensing mechanism coupled to the support platform indicative of a present configuration of the adjustable stability varying mechanism.

13. A system for training an individual comprising:
a support platform configured to support an individual for training, and tiltable in response to contraction of a muscle in the individual's body redistributing the individual's body weight upon the support platform;

a plurality of sensing mechanisms, wherein the plurality of sensing mechanisms includes a first sensor configured to monitor a tilt parameter of the support platform, a second sensor configured to monitor a muscle activity parameter of the muscle, and a third sensor configured to monitor an ankle joint angle parameter in the individual;

an electrical stimulation mechanism configured to electrically stimulate a spinal reflex pathway in the individual; and a computing device configured to receive data from the plurality of sensing mechanisms indicative of a training suitability state of the individual, and being in control communication with the electrical stimulation mechanism;

the computing device being further configured to command electrical stimulation of the spinal reflex pathway responsive to the data, such that the muscle reflexively contracts to tilt the support platform, and to record a value indicative of an amplitude of the reflexive contraction.

14. The system of claim 13 wherein the tilt parameter includes a tilt angle about a horizontal axis defined by the support platform, and the data includes data indicating the tilt angle is within a suitable range of tilt angles.

15. The system of claim 13 further comprising an adjustable stability varying mechanism for the support platform, and a third sensor coupled with the support platform and configured to monitor a stability state thereof as determined by the adjustable stability varying mechanism.

16. The system of claim 14 wherein the support platform further includes a deck having an upper standing surface for supporting the individual thereon, a lower surface, and a first and a second elongate support bar mounted to the lower surface and having a clearance there between, and wherein the adjustable stability varying mechanism includes an actuator coupled with at least one of the first and second elongate support bars and configured to adjust a size of the clearance.

17. The system of claim 13 further comprising a display, and wherein the computing device is further configured to compare the value with a second value indicative of an amplitude of a reflexive contraction occurring in response to at least one prior commanded stimulation of the spinal reflex pathway, and to output a display signal to a graphical display, responsive to the comparison.

* * * * *